US00PP23246P3

(12) United States Plant Patent
Stoppel

(10) Patent No.: US PP23,246 P3
(45) Date of Patent: Dec. 11, 2012

(54) VARIETY OF STRAWBERRY PLANT NAMED 'MALWINA'

(50) Latin Name: ***Fragaria×ananassa* (Duch.) Guedes**
Varietal Denomination: MALWINA

(76) Inventor: Peter Stoppel, Kressbronn (DE)

( * ) Notice: Subject to any disclaimer, the term of this patent is extended or adjusted under 35 U.S.C. 154(b) by 0 days.

(21) Appl. No.: 12/930,408

(22) Filed: Jan. 6, 2011

(65) Prior Publication Data

US 2012/0011626 P1 Jan. 12, 2012

Related U.S. Application Data

(60) Provisional application No. 61/399,295, filed on Jul. 9, 2010.

(51) Int. Cl.
*A01H 5/00* (2006.01)

(52) U.S. Cl. ..... Plt./208

(58) Field of Classification Search ..... Plt./208, Plt./209

See application file for complete search history.

(56) References Cited

PUBLICATIONS

GTITM UPOVROM Citation for 'MALWINA' as per QZ PBR20060617; Mar. 17, 2006.*

* cited by examiner

*Primary Examiner* — Kent L Bell
(74) *Attorney, Agent, or Firm* — The Webb Law Firm

(57) ABSTRACT

A new and distinct *Fragaria×ananassa* (Duch.) Guedes strawberry plant is provided which exhibits very strong vigor, fruits are as long as they are broad, large-sized fruits, and a very late time of ripening.

5 Drawing Sheets

Botanical classification: *Fragaria×ananassa* (Duch.) Guedes.

Varietal denomination: 'MALWINA'.

BACKGROUND OF THE INVENTION

The present invention comprises a new and distinct cultivar of strawberry plant botanically classified as *Fragaria×ananassa* (Duch.) Guedes and known by the varietal name 'MALWINA'. The new variety is also known by designation PS.01-S4. The new variety is the result of a cross between an unnamed strawberry seedling (female parent, unpatented in the United States) and 'Sophie' (male parent, unpatented in the United States). The cross resulting in 'MALWINA' occurred in 1999 in Kressbronn, Germany. The purpose of the breeding program was to develop new late harvest strawberry varieties. Subsequently, the new variety was asexually reproduced by cuttings in Kressbronn, Germany in September of 1999.

The new variety differs from its female parent in that its female parent has a brighter and softer fruit color. The new variety is similar to 'Sophie' because of its very strong vigor and compact habit. However, when compared to Sophie, 'MALWINA' is more globose, has stronger petioles, larger and darker green leaves, larger flowers, and larger and rounder fruit. Further, the new variety exhibits only a very slight difference in the shape of its primary and secondary fruits when compared to 'Sophie'.

The following table provides a detailed comparison between 'MALWINA' and the strawberry variety known as 'Florence' (unpatented in the United States):

TABLE 1

| Varietal Name | Inflorescence Position Relative to Foliage | Fruit Color | Time of Ripening (50% of Plants with Ripe Fruits) |
|---|---|---|---|
| 'MALWINA' | Beneath | Red | Very late |
| 'Florence' | Level with | Dark red | Medium to late |

The following characteristics also distinguish the new variety from other strawberry varieties known to the breeder:

Globose plant habit;

Very strong vigor;

Fruits are as long as they are broad;

Large-sized fruits; and

Very late time of ripening.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and time of year.

DESCRIPTION OF THE PLANT

Figure 1:
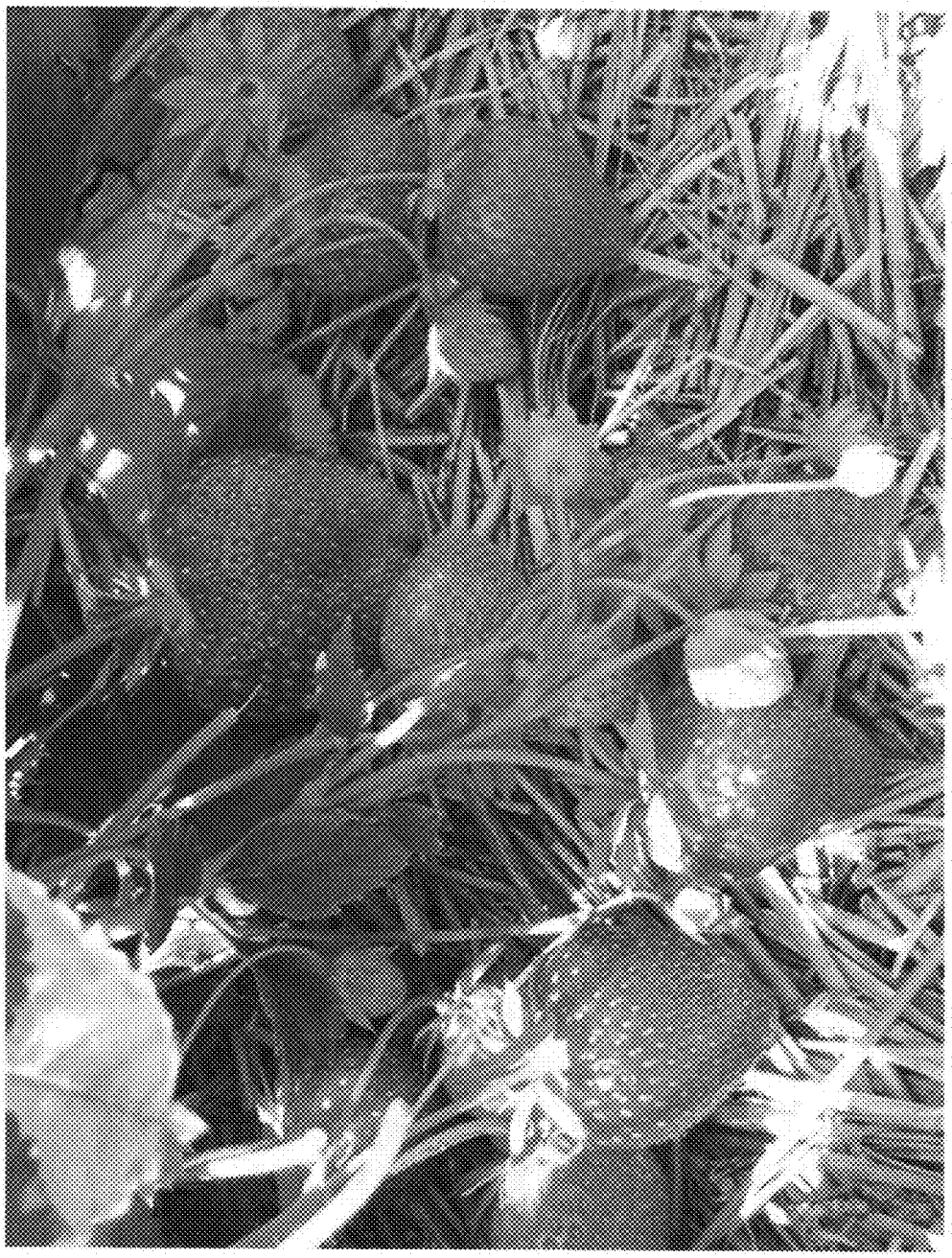
FIG. 1 is a photograph of multiple fruits of the new variety.
Figure 2:
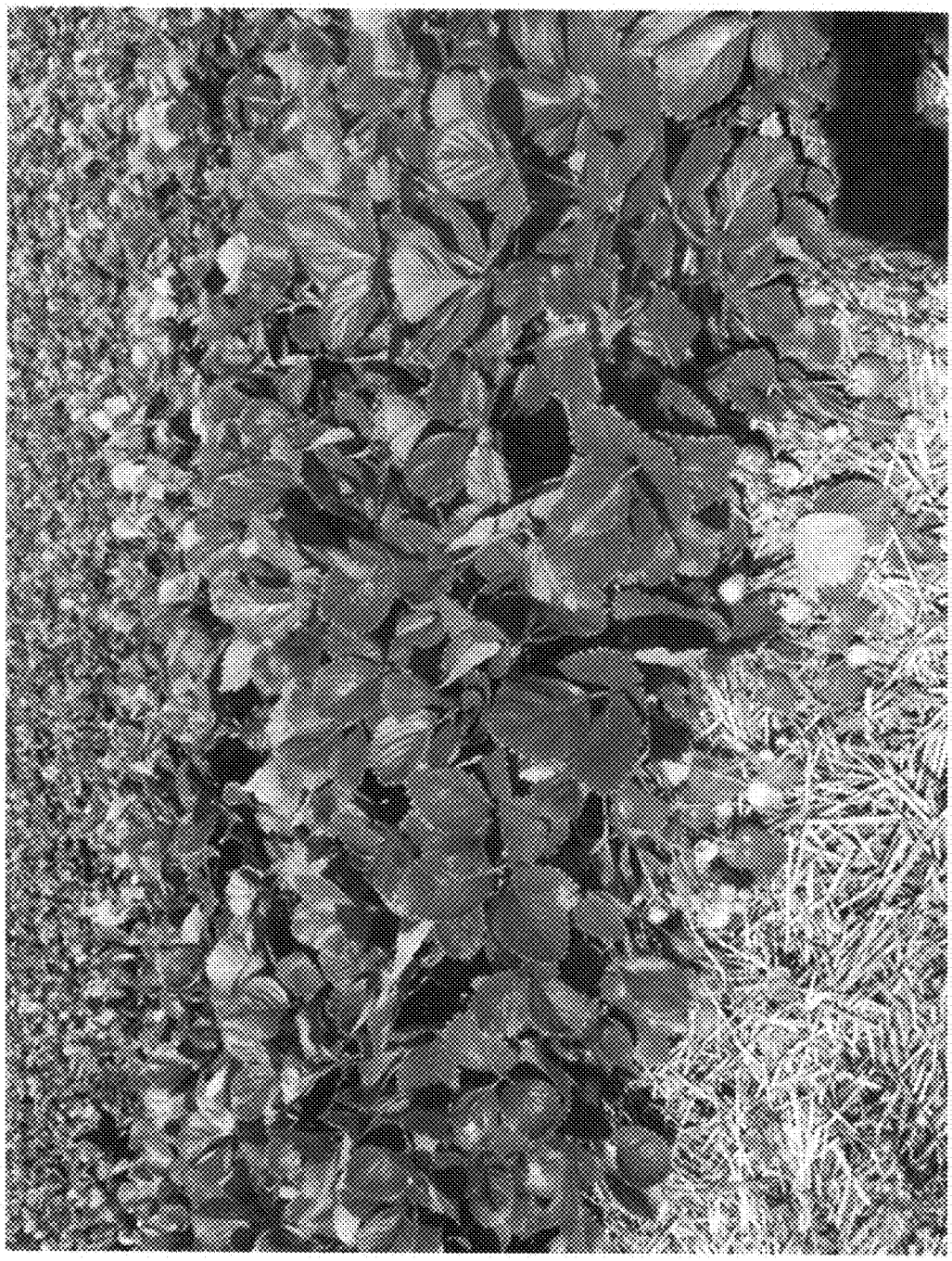
FIG. 2 is a photograph of a field of the new variety.
Figure 3:
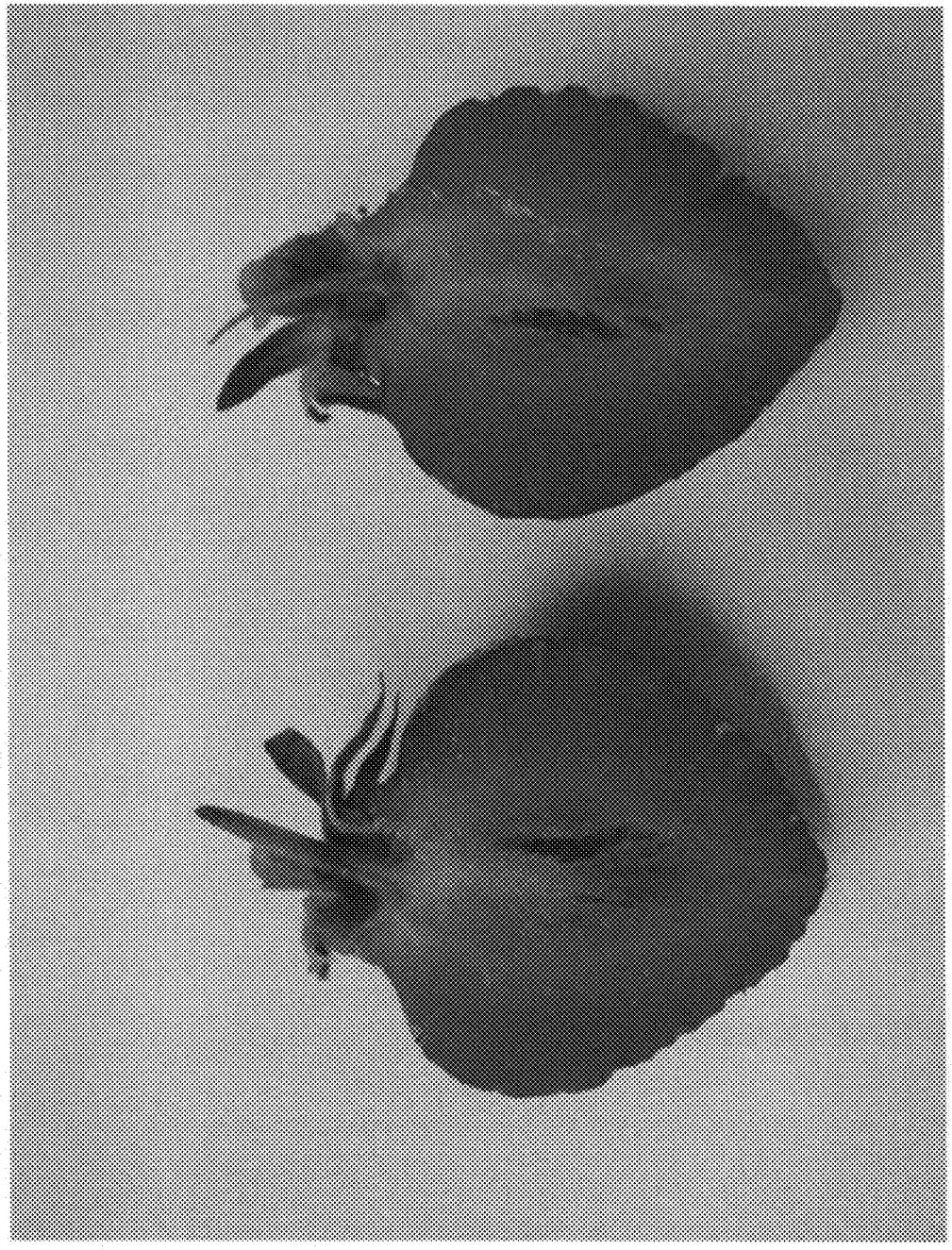
FIG. 3 is a photograph of a sliced fruit of the new variety.
Figure 4:
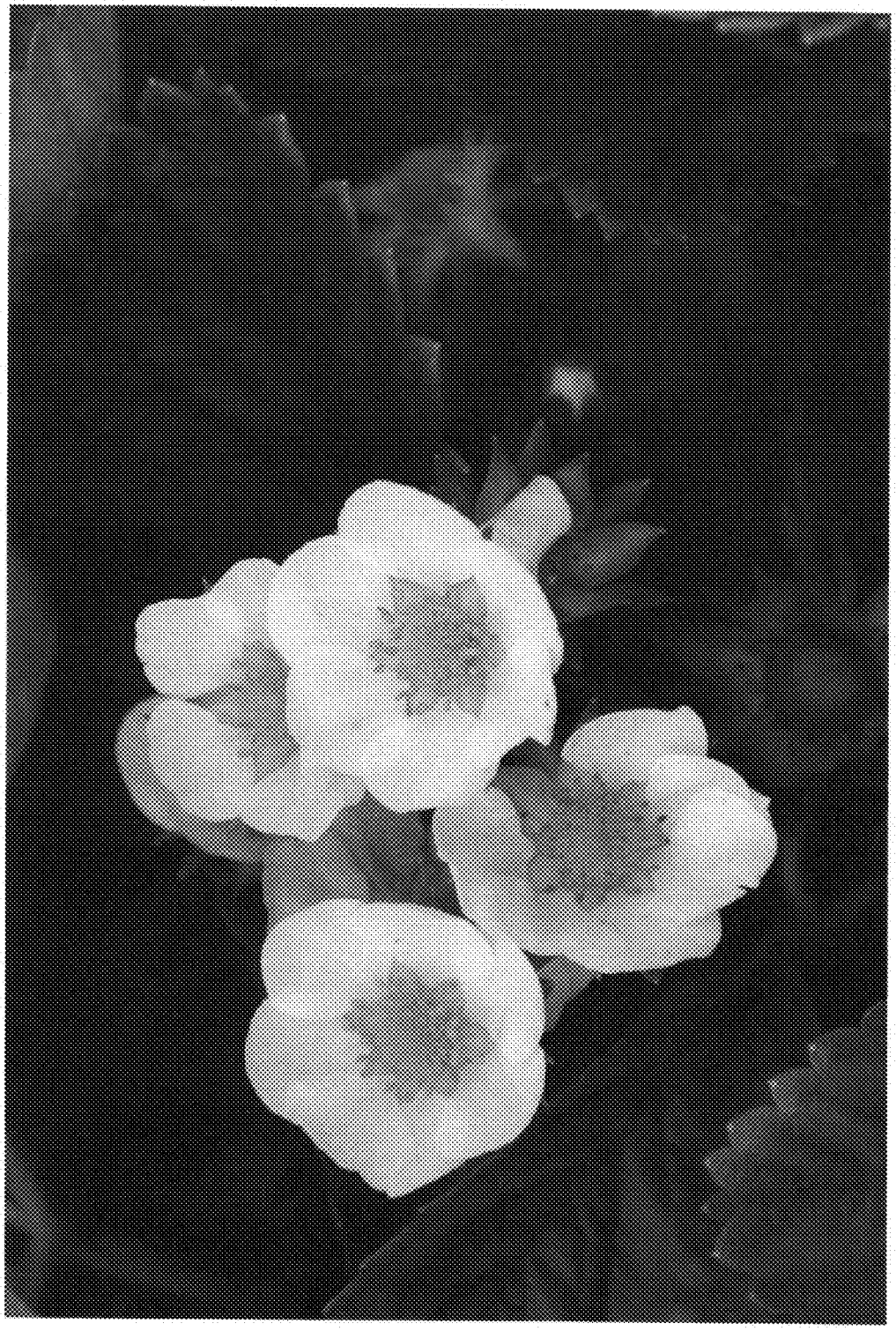
FIG. 4 is a photograph of the blossoms of the new variety.
Figure 5:
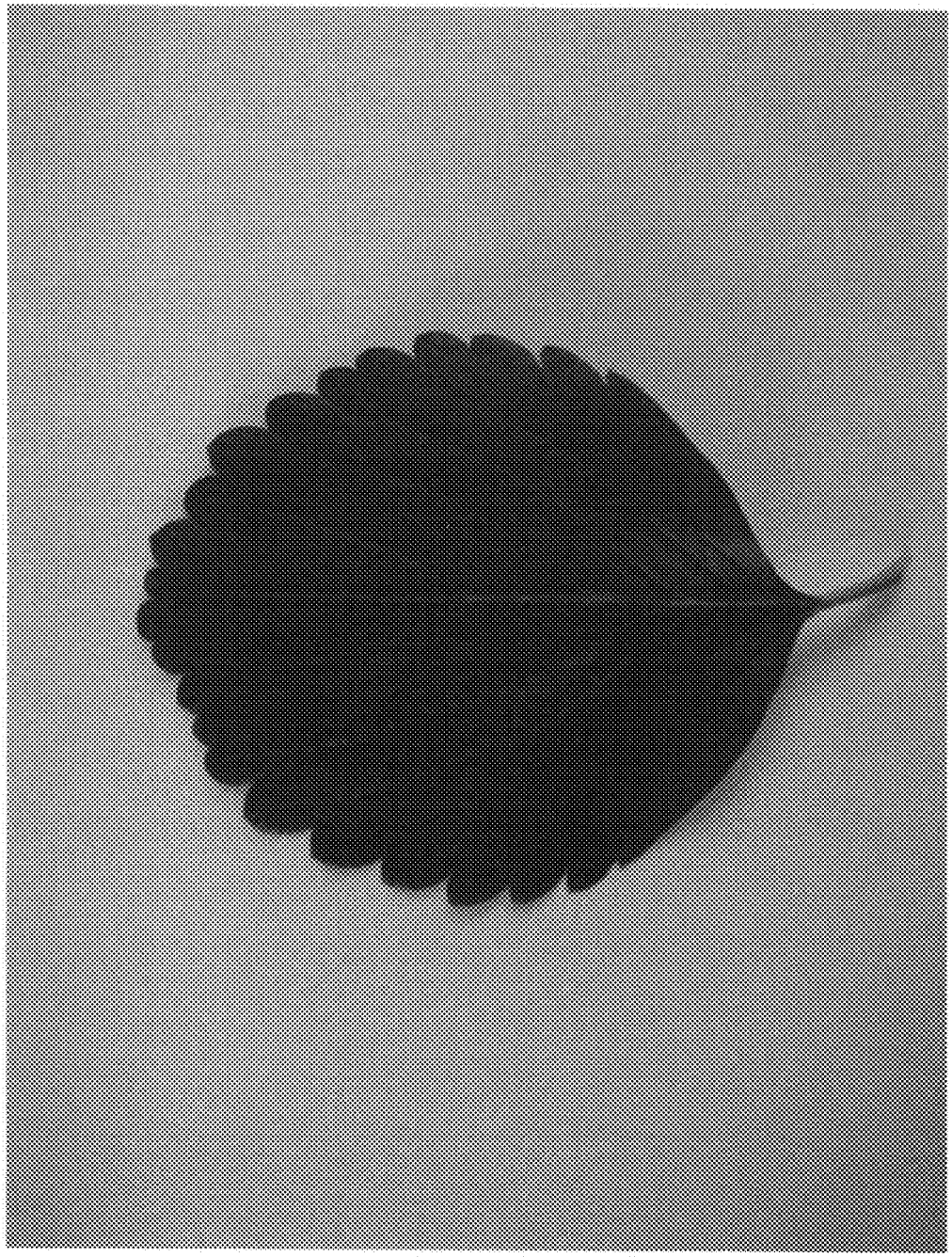
FIG. 5 is a photograph of a leaf of the new variety.

The following detailed description sets forth the characteristics of the new cultivar. The new variety was grown under natural field conditions in Kressbronn, Germany. Plants were grown in a dry and hot climate with an average day temperature of 30° C. and an average night temperature of 13° C. The new variety was almost one year old from planting when described. Color references are primarily to The R.H.S. Colour Chart of The Royal Horticultural Society of London and were identified under natural light.

BOTANICAL DATA

Time to initiate roots: 48 hours at an average temperature of 20° C.

Time to produce a rooted plant: 30 days at an average temperature of 20° C.

Rooting habit: Vigorous.

Plant form: Globose.

Height (from soil to top of plant): 30-40 cm.

Plant diameter: 35-45 cm.

Vigor: Very strong.

Disease/pest resistance: Susceptible to flower thrips and gets a bit of leaf spot. Moderately resistant to grey fruit mold and powdery mildew. Resistant to verticilium and strong against root diseases.

Weather tolerance: Very robust to rain cracking and sunburn on fruits. Plants are winter hardy in normal middle European conditions.

Foliage:

*Arrangement*.—Basal rosette; upwardly facing.

*Number of leaves per stem*.—Generally three; very rarely four.

*Petiole*.—Length: 28-33 cm. Diameter: 3-4 mm. Color: RHS 145A. Texture: Pubescence present, shooting outwards.

*Color*.—Young leaflets: Upper surface: Close to RHS 137A. Lower surface: RHS 139C. Mature leaflets: Upper surface: Close to RHS 136B. Lower surface: Close to RHS 138B.

*Lateral leaflets*.—Length: 9-10 cm. Width: 7-8 cm. Shape of leaf: Strongly concave. Shape of apex: Obtuse. Shape of base: Between acute and slightly obtuse. Texture: Very weak to absent pubescence present on both the upper and lower surfaces. Aspect: Upright. Margin type: Crenate. Anthocyanin coloration: Strong; RHS 136B.

*Terminal leaflets*.—Length: 9-12 cm. Width: 7-9 cm. Ratio length/width: Longer than broad. Shape of leaf: Strongly concave. Shape of apex: Obtuse. Shape of base: Acute. Texture: Very weak to absent pubescence present on both the upper and lower surfaces. Aspect: Upright. Margin type: Crenate.

*Whole leaf length*.—32-40 cm.

*Whole leaf width*.—14-17 cm.

*Whole leaf glossiness*.—Strong to very strong.

*Petiole*.—Length: 24.5 cm. Diameter: 3.8 to 4.5 mm. Color: RHS 145A.

*Stipule*.—Average number per leaf: 3. Length: 32.4 cm. Width: 18.1 cm. Color: RHS 137A.

*Veins*.—Venation pattern: Pinnate. Color: Upper surface: RHS 137A. Lower surface: Central portion RHS 145C, decreasing outwardly.

Fruit:

*Harvest season*.—Very late, during the middle of July in the south of Germany.

*Number of fruits per fruiting lateral*.—4-6.

*Color*.—Immature: RHS 149D. Maturing: RHS 41B. Fully mature: RHS 53A to RHS 45A (very strongly darkens at plant; edible close to RHS 187B). Evenness of color: Even.

*Taste*.—Very good.

*Length*.—3.5-4 cm.

*Width*.—3.5-4 cm.

*Length/width ratio*.—As long as is broad.

*Overall shape*.—Conical.

*Unevenness of surface*.—Absent or very weak.

*Glossiness*.—Strong.

*Weight*.—About 20 g.

*Achene position*.—Level with surface.

*Achene color*.—From RHS 151D to RHS 163B.

*Average number of achenes per berry*.—547.

*Flesh firmness*.—Medium to firm.

*Fruiting truss length*.—15-28 cm.

*Fruiting truss width*.—2-4 mm.

*Fruiting truss color*.—RHS 145A.

Reproductive organs:

*Stamens*.—Number per flower: 28-34. Size: Length: 2.5 mm. Width: 2.0 mm.

*Anthers*.—Shape: Apex: Rounded. Base: Cordate (horseshoe-shaped). Size: Length: 0.9-1.1 mm. Width: 0.8-0.9 mm. Color: Edge: Close to RHS 163B. Center: Close to RHS 14A.

*Stigma*.—Texture: Lightly papillose surface. Shape: Rounded to ovate. Color: RHS 6A.

*Style*.—Length: About 0.8 mm. Color: RHS 4A.

*Ovary*.—Texture: Pubescence present. Length: About 4.3 mm. Color: With seed: RHS 150B. Without seed: RHS 18C.

*Stolon*.—Length: Mother plant to first stolon-plant: 35-45 cm. Mother plant to second stolon-plant: 55-60 cm. Diameter: 2-4 mm. Color: RHS 145A to 145B.

Flowers:

*Position relative to the foliage*.—Beneath.

*Natural flowering season*.—Very late; at the end of June in southern Germany.

*Number of flowers per plant*.—40-50.

*Fully opened color*.—Upper surface: RHS 155C and RHS 8C about 0.7 mm from the base. Lower surface: RHS 155C.

*Fragrance*.—None present.

*Longevity*.—2-3 days.

*Flower description*.—Rotate flowers arranged singly at lateral apices; 5-6 petals; flat outspreading; slightly overlapping; terminal.

*Flower height*.—5-6 mm.

*Flower diameter*.—Medium to large; about 1.9-2.3 cm.

*Petal*.—Count: Single whorl of 5-6 petals. Shape: Compressed; slightly elliptic to obovate. Length: 9-10 mm. Width: 10-11 mm. Apex: Rounded. Base: Symmetric; broad; wedge-shaped; convex; broader than long. Margin: Entire. Texture: Upper and lower surfaces: Smooth; glabrous; glossy.

*Sepals*.—Length: Internal: 10 mm. External: 7.5 mm. Width: Internal: 4.9 mm. External: 3.3 mm. Shape: Lanceolate. Arrangement: A single whorl of two star-shaped circles — calyx of sepals, each with about 5-6 sepals. Internal sepals are broader and longer than external sepals, all slightly overlapping; calyx situated in a basin. Number: A total of 10-13. Apex: Acute. Color: Mature sepals: Upper surface: Internal: RHS 145A. External: RHS 145A. Lower surface: Internal: RHS 145A. External: RHS 137A (lightens toward the base). Young sepals: Upper surface: RHS 145A. Lower surface: Close to RHS 145A. Margin: Entire. Texture: Upper and lower surfaces: Pubescence present.

*Buds*.—Length: About 8 mm. Diameter: About 9 mm. Shape: Broader than longer; rounded. Apex: Acute. Color: RHS 145A.

I claim:

1. A new and distinct variety of *Fragaria×ananassa* (Duch.) Guedes strawberry plant substantially as is herein described and illustrated.

* * * * *